(12) United States Patent
Williams

(10) Patent No.: US 11,090,113 B2
(45) Date of Patent: Aug. 17, 2021

(54) MICROWAVE ABLATION ANTENNA ASSEMBLIES

(71) Applicant: Gyrus Medical Limited, Cardiff (GB)

(72) Inventor: David Nicholas Williams, Caerphilly (GB)

(73) Assignee: Gyrus Medical Limited, Cardiff (GB)

(*) Notice: Subject to any disclaimer, the term of this patent is extended or adjusted under 35 U.S.C. 154(b) by 390 days.

(21) Appl. No.: 15/958,219

(22) Filed: Apr. 20, 2018

(65) Prior Publication Data

US 2018/0325590 A1 Nov. 15, 2018

(30) Foreign Application Priority Data

May 11, 2017 (GB) .................................. 1707576

(51) Int. Cl.
| | | |
|---|---|---|
| *A61B 18/12* | (2006.01) | |
| *A61B 18/14* | (2006.01) | |
| *A61B 18/18* | (2006.01) | |
| *A61B 18/00* | (2006.01) | |

(52) U.S. Cl.
CPC .......... *A61B 18/18* (2013.01); *A61B 18/1815* (2013.01); *A61B 2018/00577* (2013.01); *A61B 2018/1853* (2013.01); *A61B 2018/1869* (2013.01); *A61B 2018/1892* (2013.01)

(58) Field of Classification Search
CPC ................ A61B 18/18; A61B 18/1815; A61B 2018/1892; A61B 2018/1838
See application file for complete search history.

(56) References Cited

U.S. PATENT DOCUMENTS

| | | | | |
|---|---|---|---|---|
| 5,301,687 A | * | 4/1994 | Wong ................. | A61B 18/1815 606/33 |
| 2012/0029503 A1 | | 2/2012 | Bonn | |
| 2016/0030112 A1 | * | 2/2016 | Brannan ................ | A61B 18/18 606/33 |
| 2016/0095657 A1 | | 4/2016 | Brannan | |

OTHER PUBLICATIONS

Powys, Colin; "UK Search Report"; prepared for application No. GB1707576.3; dated Oct. 23, 2017; 3 pages.

* cited by examiner

*Primary Examiner* — Daniel W Fowler
*Assistant Examiner* — Tigist S Demie
(74) *Attorney, Agent, or Firm* — Winstead PC

(57) ABSTRACT

A microwave ablation antenna assembly (20) incorporates a choke assembly (40) having a dielectric element (42) and a conducting element (48). The conducting element (48) is chosen from a group of elements of fixed length, but with differing electrical lengths for providing cancellation properties for different wavelengths of microwave energy.

4 Claims, 5 Drawing Sheets

MICROWAVE ABLATION ANTENNA ASSEMBLIES

The present invention relates to microwave ablation antenna assemblies.

BACKGROUND OF THE INVENTION

In the treatment of tumours, for example tumours caused by a disease such as cancer, it is known to use microwave ablation techniques to ablate the tumour. Such microwave ablation techniques typically ablate the targeted tissue by delivering a controlled amount of microwave energy into the tumour.

Minimally-Invasive techniques for delivering such microwave energy have been shown to be effective in the treatment of tumours. In a minimally-invasive technique, a microwave emitter is inserted directly into a point of treatment, either using a normal body orifice or via percutaneous insertion. Such minimally-invasive procedures and devices provide a means of treating tumours in patients who either cannot undergo other forms of treatment (e.g. radiotherapy, surgical resection, chemotherapy) or where ablation is preferred as a therapy.

One type of commonly used microwave antenna assembly includes a dipole antenna, which consists of a coaxial construction having an inner conductor and an outer conductor with a dielectric junction (feed point) separating a portion of the inner conductor. The inner conductor may be coupled to a portion corresponding to a first dipole radiating portion, and a portion of the outer conductor may constitute a second dipole radiating portion. The dipole radiating portions may be configured such that one radiating portion is located proximally of the dielectric junction (known as the feed-point), and the other portion is located distally of the dielectric junction.

The dipole antenna is connected to a source of microwave energy using a coaxial conductor assembly, the antenna and coaxial feed will be described in more detail below.

In order for such a device to be controlled properly, and to improve the delivery of microwave energy into the tissue being treated, it is desirable for the antenna assembly to be impedance matched with the microwave energy generator. An ablation shape as close to spherical as possible is also desirable. Existing designs of antenna assemblies can be improved upon in these respects.

SUMMARY OF THE INVENTION

According to the present invention, there is provided a microwave ablation antenna assembly comprising an elongate body which extends from a first end to a second end thereof, and which defines therein a hollow inner volume and a longitudinal axis of the antenna; an applicator tip portion mounted on the second end of the elongate body; an elongate coaxial conductor assembly for connection to a source of microwave energy having an operating frequency in the microwave frequency band, the coaxial conductor assembly extending from the first end of the body towards the second end of the body through the inner volume, the coaxial conductor assembly having an inner conductor, a dielectric layer arranged radially outwardly of the inner conductor and extending along the inner conductor, and an outer conductor arrange radially outwardly of the dielectric layer and extending along the dielectric layer, the inner conductor defining a signal feed-point of the coaxial conductor assembly at a distal end thereof towards the second end of the body; a dipole tip portion which extends from the feed point of the coaxial conductor assembly towards the applicator tip, and which is electrically connected with the inner conductor of the coaxial conductor assembly; and a choke assembly including a choke dielectric element of dielectric material arranged adjacent, and coaxially with, the coaxial conductor assembly such that the conductor assembly passes through the choke dielectric element, the choke dielectric element being spaced apart from the feed point of the coaxial conductor assembly and defining an outer surface, and a choke conducting element of electrically conductive material, the conducting element having a first portion arranged adjacent, and coaxially with, the coaxial conductor assembly, between the choke dielectric element and the feed point, the having a second portion which is contiguous with the first portion and which extends from the first portion towards the first end of the body, adjacent the outer surface of the choke dielectric element, wherein the first and second portions of the choke conducting element have respective first and second lengths in the axial direction of the body, the second length providing an electrical length substantially equal to one quarter of the wavelength of such microwave energy to be transmitted by the coaxial conductor assembly, and wherein the sum of the first and second lengths is constant and independent of the wavelength of such microwave energy.

In one example, such an antenna assembly is for use in the microwave frequency band for frequencies from 0.9 GHz to 10 GHz.

As the effective permittivity seen by the antenna is in part determined by the tissue surrounding the device, this means the physical length of the tuned dipole element may not be the same as the physical length of the choke internal dimension, if a high permittivity ceramic dielectric is used internally for the choke. In order to tune the cancellation effect, either the permittivity of the dielectric within the choke has to be varied, or alternatively the internal physical length of the choke can be varied by varying the length of a conductive collar. The latter allows standard materials to be used.

Such an antenna assembly is able to make use of a large number of standard components, whilst being individually tuned for the microwave energy being emitted by the assembly.

In one example, the body is cylindrical, and the coaxial conductor assembly, dipole tip portion and choke assembly extend substantially centrally through the inner volume of the body.

In one example, a dielectric fluid is provided in the inner volume of the body. Such a fluid provides improved cooling for the assembly.

According to a second aspect of the present invention, there is provided a method of manufacturing a microwave ablation antenna assembly comprising an elongate body which extends from a first end to a second end thereof, and which defines therein a hollow inner volume and a longitudinal axis of the antenna; an applicator tip portion mounted on the second end of the elongate body; an elongate coaxial conductor assembly for connection to a source of microwave energy having an operating frequency, the coaxial conductor assembly extending from the first end of the body towards the second end of the body through the inner volume, the coaxial conductor assembly having an inner conductor, a dielectric layer arranged radially outwardly of the inner conductor and extending along the inner conductor, and an outer conductor arrange radially outwardly of the dielectric layer and extending along the dielectric layer, the inner conductor defining a signal feed-point of the coaxial conductor assembly at a distal end thereof towards the second end of the body; a dipole tip portion which extends from the feed point of the coaxial conductor assembly towards the applicator tip, and which is electrically connected with the inner conductor of the coaxial conductor assembly; and a choke assembly including a choke dielectric element of dielectric material arranged adjacent, and coaxially with, the coaxial conductor assembly such that the conductor assembly passes through the choke dielectric element, the choke dielectric element being spaced apart from the feed point of the coaxial conductor assembly and defining an outer surface, and a choke conducting element of electrically conductive material, the conducting element having a first portion arranged adjacent, and coaxially with, the coaxial conductor assembly, between the choke dielectric element and the feed point, the having a second portion which is contiguous with the first portion and which extends from the first portion towards the first end of the body, adjacent the outer surface of the choke dielectric element, wherein the first and second portions of the choke conducting element have respective first and second lengths in the axial direction of the body, the second length being substantially equal to one quarter of the wavelength of such microwave energy to be transmitted by the coaxial conductor assembly, and wherein the sum of the first and second lengths is constant and independent of the wavelength of such microwave energy, the method comprising the steps of determining the wavelength of the microwave energy to be emitted by the antenna assembly being manufactured; from the determined wavelength, determining the length of the second portion of the choke conducting element required for high impedance, microwave cancellation (i.e. ¼ wavelength); selecting the choke conducting element having the second portion of the required determined length, from a group of fixed overall length choke conducting elements; and manufacturing the antenna assembly using standard components in combination with the selected choke conducting element.

In one example, such a method further comprises the step of manufacturing a group of choke conducting elements having a fixed overall length, with differing first and second length combinations.

DETAILED DESCRIPTION OF THE PREFERRED EMBODIMENTS

Figure 1:
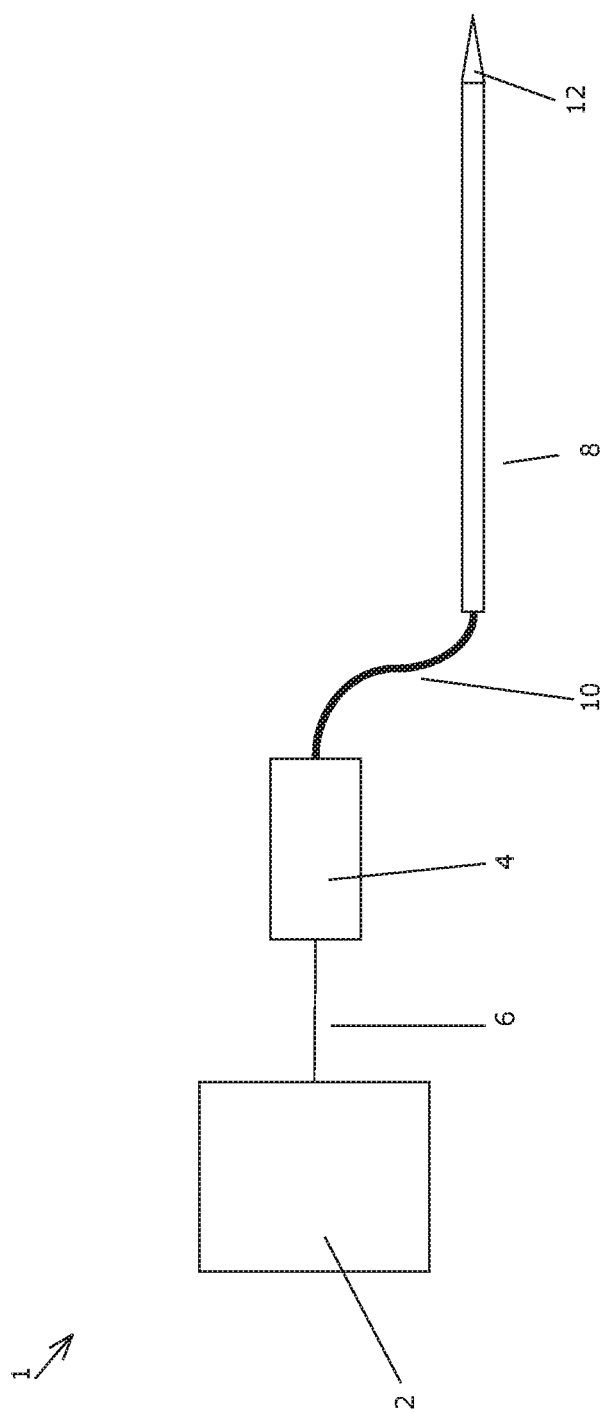
FIG. 1 is a schematic block diagram of a microwave ablation system.

FIG. 1 is a schematic diagram illustrating a microwave ablation system 1 comprising a controller unit 2, and a microwave power generator 4 which is connected to the controller via a control connection 6. An ablation antenna assembly 8 is connected to the microwave power generator 4 via a power connection 10. The antenna assembly includes a tip portion 12 which aids insertion of the antenna assembly into the tissue being treated, and enables a desired output pattern of microwave energy from the antenna assembly.

The controller unit 2 is operable to control the power generator 4 to supply the correct magnitude and operating frequency of microwave energy to the antenna assembly 8. Different control schemes are known in the art, and will not be described here for the sake of brevity. The present invention is concerned with the design of the antenna assembly, and such an assembly may be used with any appropriate control scheme and control hardware.

Figure 2:
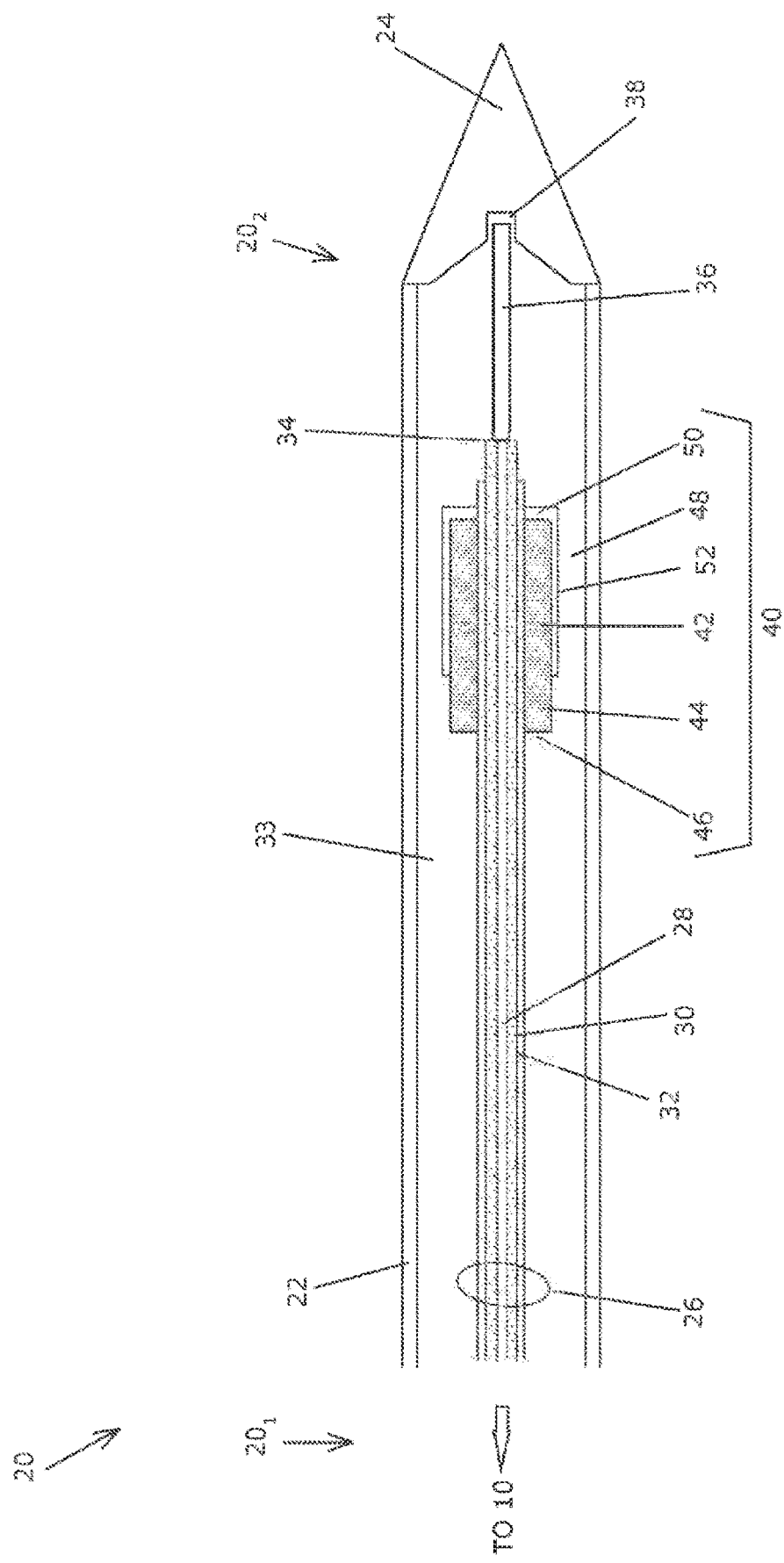
FIG. 2 is a cross sectional view of part of a microwave ablation antenna assembly embodying a first aspect of the present invention.

FIG. 2 is a cross-sectional view of part of an antenna assembly 20 embodying the present invention. The antenna assembly 20 comprises a body 22, which is preferably cylindrical in form. The body 22 extends from a first (proximal) end $20_1$ to a second (distal) end $20_2$, and defines a longitudinal axis of the assembly. The body 22 defines an inner volume, in which most of the other components of the assembly are housed. The body 22 provides the assembly with the necessary rigidity for insertion into the tissue being treated. The body 22 is preferably of a rigid material, such as a composite material (for example glass fibre, carbon fibre, aramid fibre), stainless steel, other biocompatible metals (e.g. titanium) or combinations of, and is typically 1.5 to 3 mm mm in diameter.

An applicator tip 24 is attached to the second end $20_2$ of the body, to close off the inner volume at the second end. The applicator tip is preferably a faceted trocar and has a relatively sharp distal end point. The applicator tip 24 is designed to be suitable for insertion into the tissue being treated, and partly to affect the transmission pattern for microwave energy into that tissue. It also forms a water tight seal to the internal volume of the body 22.

A coaxial conductor assembly 26 extends along the inner volume of the body 22 from the first end $20_1$ towards the second end $20_2$. The coaxial conductor assembly 26 is connectable, at a proximal end thereof, to the microwave energy generator 4 of FIG. 1. The coaxial conductor assembly 26 extends substantially along the longitudinal axis of the body 22, and comprises an inner conductor 28. The inner conductor 28 is of an electrically conductive material such as copper. Surrounding the inner conductor 28 is a dielectric layer 30 which extends along the inner conductor 28, radially outwardly thereof. The dielectric layer 30 is of any appropriate dielectric material. Surrounding the dielectric layer 30, is an outer conductor 32, which is of an electrically conductive material such as copper. The outer conductor 32 extends along the dielectric layer 30, radially outwardly thereof. Typically, the inner conductor 28 is a wire having a circular cross section, such that the dielectric layer 30 is a cylinder of dielectric material surrounding an outer surface of the inner conductor 28. The outer conductor 32 is then formed by a cylinder of electrically conductive material surrounding an outer surface of the dielectric layer 30.

The inner conductor 28 defines a signal feed-point 34 at its distal end (that is, the end towards the second end $20_2$ of the body 22). A dipole tip portion 36 extends longitudinally from the distal end of the coaxial conductor assembly 36 into a reception aperture in the applicator tip 24. The reception aperture 38 is located centrally with respect to the longitudinal axis of the assembly within the applicator tip 24. The reception aperture 38 is designed so as to locate centrally the dipole tip portion 36 into the tip 24. The tip material is chosen for it mechanical and electrical properties, which have to be considered in the design.

The dielectric layer 30 extends along the complete length of the inner conductor 28 to the distal end thereof adjacent the dipole tip portion 36. The outer conductor 32 stops short of the distal end of the inner conductor 28 and dielectric layer 32, and so is spaced apart longitudinally from the signal feed-point 34 and dipole tip portion 36.

A dielectric fluid 33 may be provided within the inner volume of the body 20 in order to provide a key functional element to the microwave design and also provide a cooling fluid for the antenna assembly. This fluid will typically be isotonic saline or deionised water.

The antenna assembly includes a choke (or balun) assembly 40 which acts to convert an unbalanced microwave input signal into a balanced signal suitable for driving a dipole antenna. Without this conversion, the shape of the ablated tissue extends up the shaft of the instrument and affects tissue which is outside the desired ablation zone. The choke assembly 40 also acts to minimise power reflected back to the microwave source.

The choke assembly 40 is located within the body 22, around the coaxial conductor assembly 26, spaced apart from the distal end of the coaxial conductor assembly 26. The choke assembly 40 comprises a choke dielectric element 42 which extends around a portion of the outer conductor 32. The choke dielectric element 42 is adjacent and coaxial with the coaxial conductor assembly 26, and is spaced apart from the feed point 34 of the conductor assembly. In the case when the coaxial conductor assembly 26 has a circular cross section, the choke dielectric element 42 is in the form of a cylinder of dielectric material surrounding an outer surface of the outer conductor 32 of the coaxial conductor assembly 26. The choke dielectric element 412 has a proximal end 46 towards the first end $20_1$ of the body 22 and a distal end towards the second end $20_2$ of the body 22.

The choke assembly 40 also includes a choke conducting element 48 of an electrically conductive material having a first portion 50 which is arranged adjacent, and coaxial with, the conductor assembly 26, between the choke dielectric element 42 and the feed point 34. The choke conducting element 48 has a second portion 52 which extends from the first portion 48 coaxially with the conductor assembly 26 and choke dielectric element 42 in a direction towards the first end $20_1$ of the body 22. The second portion 52 of the choke conducting element 48 extends adjacent an outer surface of the choke dielectric element 42, and surrounds that element 42.

The choke conducting element 48 acts as the proximal leg of the dipole antenna. Signal cancellation takes place at the proximal edge of the choke conducting element 48 between the direct signal, and the signal which runs around the inside of the choke conducting element 48, if the round-trip distance equals $\lambda/2$ (where $\lambda$ is the wavelength of the microwave signal). This round-trip distance can be achieved by setting the length of the second portion 52 of the choke conducting element 50 to be equal to $\lambda/4$. When the second portion length is set appropriately to provide this effective electrical length, a high impedance is presented to microwaves which would otherwise be transmitted towards the first end $20_1$ of the body 22. The effect of this high impedance is to confine the microwave radiation to give a more spherical ablation shape.

As the effective permittivity seen by the dipole antenna is in part determined by the tissue surrounding the device, this affects the propagation velocity and therefore dipole dimensions. In order to tune the cancellation effect, either the permittivity of the dielectric element 42 within the choke assembly needs to be varied, or the internal conducting length of the choke assembly 40 may be varied. In an embodiment of the present invention, the lengths of the first and second portions of the choke conducting element 48 are set in order to tune the choke assembly cancellation effect for the particular microwave frequency being used. The effective electrical length of the second portion 52 of the choke conducting element 48 is determined by the physical length of the second portion 52, the permittivity of the choke dielectric element 42 and the tissue in which the device is being used. The physical length of the second portion 52 is chosen in dependence upon the two other factors, and on the microwave frequency being used, and this then determines the length of the first portion 52, such that the overall length of the choke conducting element 48 is fixed.

Figure 3:
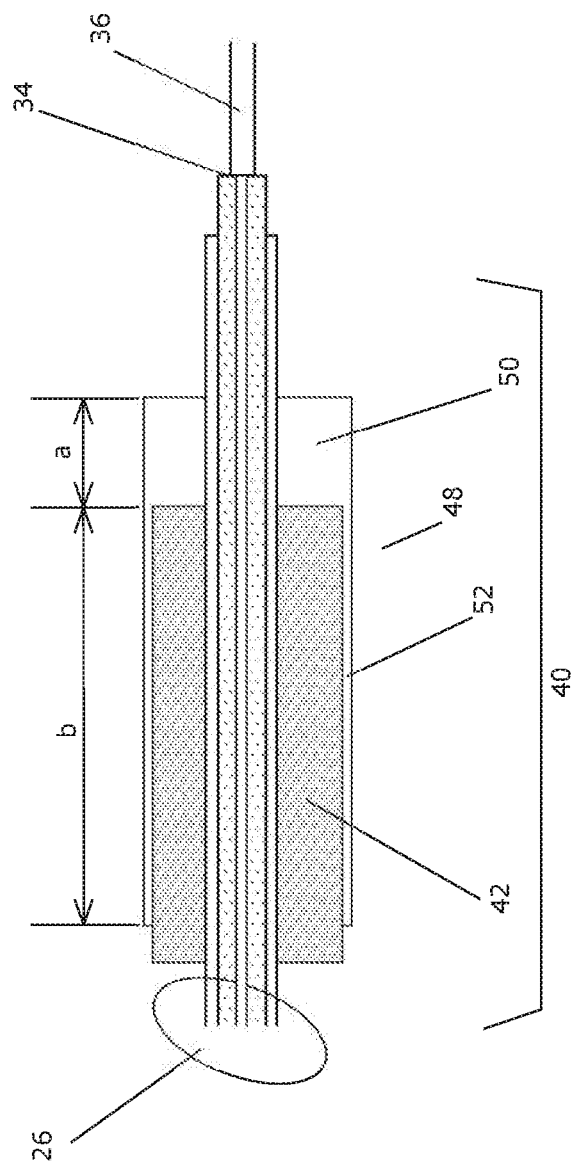
FIG. 3 is an enlarged cross sectional view of a portion of the part of the microwave ablation antenna assembly of FIG. 2.

FIG. 3 illustrates the choke assembly 40 used in an embodiment of the present invention in more detail. As described above, the choke assembly 40 includes a choke dielectric element 42 of dielectric material arranged adjacent, and coaxially with, the coaxial conductor assembly 26. The conductor assembly 26 passes through the choke dielectric element 42. The choke dielectric element 42 is spaced apart from the feed point 34 of the coaxial conductor assembly 26. The choke dielectric element 42 defines an outer surface which extends longitudinally.

The choke assembly 40 includes a choke conducting element 48 of electrically conductive material. The choke conducting element 48 has a first portion 50 arranged adjacent, and coaxially with, the coaxial conductor assembly 26, between the choke dielectric element 42 and the feed point 34. The choke conducting element 48 also includes a second portion 52 which is contiguous with the first portion 50 and which extends from the first portion 50 towards the first end $20_1$ of the body 22, adjacent the outer surface of the choke dielectric element.

The first and second portions 50, 52 of the choke conducting element 48 have respective first and second lengths a, b in the axial direction of the body 22. The second length b is chosen in dependence upon the wavelength of the microwave energy to be transmitted by the coaxial conductor assembly 26. That is, the second length b is chosen such that the second portion 52 of the choke conducting element 48 has an effective electrical length equal to $\lambda/4$ (¼ wavelength) of the microwave energy to be transmitted; this effective electrical length is determined by the permittivity of choke dielectric, 42. In an embodiment of the present invention, the sum a+b of the first and second lengths a, b is constant and independent of the wavelength of the microwave energy. In such an embodiment, the overall length of the choke conducting element is, therefore, fixed for all practical choices of microwave wavelength. The effective electrical length of the second portion is determined by the permittivity of the choke dielectric element 42 and the tissue into which the device is inserted during use.

The standard fixed length of the choke assembly 40 means that all other components of the antenna assembly 20 can be standardised. The choke dielectric element 42 may be of fixed length for different applications, since the choke dielectric element 42 may extend out of the choke conducting element 48 in the direction of the first end $20_1$ of the body 22. In addition, such a design allows the material used for the choke dielectric to be standardised across a range of microwave frequencies, such that a range of devices has a dielectric material of the same permittivity. The length of the second portion 52 of the choke conducting element 48 can be adjusted to provide the appropriate effective electrical length for the particular application of the device concerned.

Figure 4B:
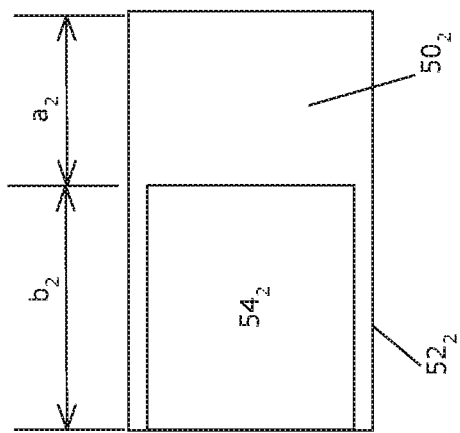
FIG. 4a and FIG. 4b illustrate respective examples of a component of the assembly of FIG. 3.
Figure 4A:
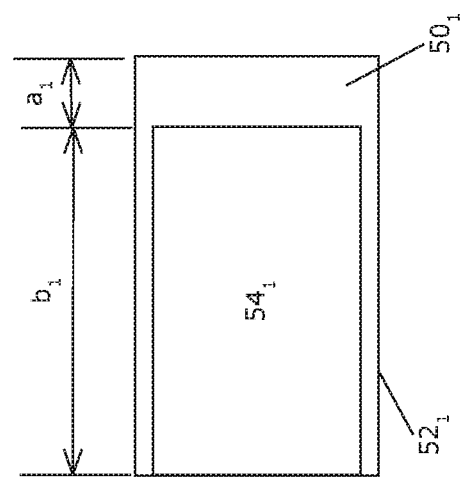

FIG. 4a and FIG. 4b illustrate respective examples of choke conducting elements 48. The example of FIG. 4a has a first portion $50_1$ having a first length $a_1$ and a second portion $52_1$ having a second length $b_1$. The example of FIG. 4b has a first portion $50_2$ having a first length $a_2$ and a second portion $52_2$ having a second length $b_2$. The second portions $52_1$ and $52_2$ define respective apertures $54_1$ and $54_2$ for reception of the choke dielectric element 42.

In the examples, $b_1 > b_2$, such that the first example is for use with microwave energy having a longer wavelength than that of the second example, and/or with an internal dielectric of higher permittivity. However, the overall lengths of the two example are equal: $a_1+b_1=a_2+b_2$. This composite length can be chosen to provide an optimised wavelength/4 electrical distance for the proximal section of the dipole antenna. The electrical length of this diopole section is a function of the permittivity of the surrounding dielectric material and tissue being treated.

Figure 5:
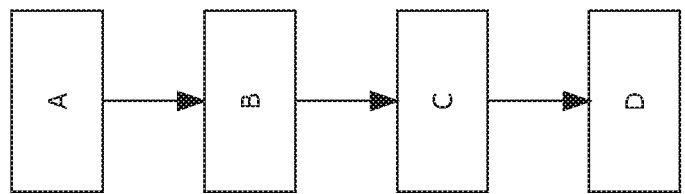
FIG. 5 illustrates steps in a method embodying another aspect of the present invention.

FIG. 5 illustrates steps in a method embodying another aspect of the present invention. Such a method relates to the manufacture of an ablation antenna assembly embodying the first aspect of the present invention, and includes the steps of:
A. Determining the wavelength of the microwave energy to be emitted by the antenna assembly being manufactured;
B. From the determined wavelength and permittivity value of the choke dielectric element, determining the length (b) of the second portion of the choke conducting element required for high impedance, microwave cancellation (i.e. ¼ wavelength);
C. Selecting the choke conducting element having the second portion of the required determined length, from a group of fixed overall length choke conducting elements;
D. Manufacture the antenna assembly using standard components in combination with the selected choke conducting element.

In advance of the steps described above, a manufacturing method embodying the present invention may also include manufacturing a group of choke conducting elements having a fixed overall length, with differing first and second length combinations.

The invention claimed is:

1. A microwave ablation antenna assembly for delivery of microwave energy of selected wavelength, the microwave ablation assembly comprising:
an elongate body which extends from a first end to a second end thereof, and which defines therein a hollow inner volume and a longitudinal axis;
an applicator tip portion mounted on the second end of the elongate body;
an elongate coaxial conductor assembly for connection to a source of microwave energy and having an operating frequency in a microwave frequency range, the elongate coaxial conductor assembly extending from the first end of the elongate body towards the second end of the elongate body through the hollow inner volume, the elongate coaxial conductor assembly having an inner conductor, a dielectric layer arranged radially outwardly of the inner conductor and extending along the inner conductor, and an outer conductor arrange radially outwardly of the dielectric layer and extending along the dielectric layer, the inner conductor defining a signal feed-point of the elongate coaxial conductor assembly at a distal end thereof towards the second end of the elongate body;
a dipole tip portion which extends from the signal feed point of the elongate coaxial conductor assembly towards the applicator tip, and which is electrically connected with the inner conductor of the elongate coaxial conductor assembly; and
a choke assembly including:
a choke dielectric element of dielectric material arranged adjacent, and coaxially with, the elongate coaxial conductor assembly such that the elongate coaxial conductor assembly passes through the choke dielectric element, the choke dielectric element being spaced apart from the signal feed point of the elongate coaxial conductor assembly and defining an outer surface, and a choke conducting element of electrically conductive material, the choke conducting element having a first portion arranged adjacent, and coaxially with, the elongate coaxial conductor assembly, between the choke dielectric element and the signal feed point, the choke conducting element having a second portion which is contiguous with the first portion and which extends from the first portion towards the first end of the elongate body, adjacent the outer surface of the elongate choke dielectric element,
wherein the first and second portions of the choke conducting element have respective first and second lengths in an axial direction of the elongate body, the second length providing an electrical length equal to one quarter of the selected wavelength of microwave energy to be transmitted by the elongate coaxial conductor assembly, and wherein a sum of the first and second lengths is constant and independent of the selected wavelength of microwave energy.

2. The microwave ablation antenna assembly as claimed in claim 1, wherein the elongate body is cylindrical, and the elongate coaxial conductor assembly, dipole tip portion and choke assembly extend centrally through the inner volume of the elongate body.

3. The microwave ablation antenna assembly as claimed in claim 1, further comprising a dielectric fluid in the hollow inner volume of the elongate body.

4. The microwave ablation antenna assembly as claimed in claim 1, wherein the microwave frequency range is 0.9 GHz to 10 GHz.

* * * * *